(12) United States Patent
Bechtold-Peters et al.

(10) Patent No.: US 7,070,800 B2
(45) Date of Patent: Jul. 4, 2006

(54) INHALABLE POWDER CONTAINING TIOTROPIUM

(75) Inventors: Karoline Bechtold-Peters, Biberach (DE); Michael Walz, Bingen (DE); Georg Boeck, Mainz (DE); Rolf Doerr, Ober-Olm (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 103 days.

(21) Appl. No.: 09/975,418

(22) Filed: Oct. 11, 2001

(65) Prior Publication Data

US 2002/0110529 A1 Aug. 15, 2002

Related U.S. Application Data

(60) Provisional application No. 60/252,683, filed on Nov. 22, 2000.

(30) Foreign Application Priority Data

Oct. 12, 2000 (DE) .......................... 100 50 635

(51) Int. Cl.
- *A61F 13/02* (2006.01)
- *A61F 9/66* (2006.01)
- *A61F 9/14* (2006.01)
- *A61L 9/04* (2006.01)

(52) U.S. Cl. .................. 424/434; 424/46; 424/435; 424/489; 424/493; 424/451; 424/456

(58) Field of Classification Search ............... 424/489, 424/493, 46, 434, 435, 451, 456
See application file for complete search history.

(56) References Cited

U.S. PATENT DOCUMENTS

| | | | |
|---|---|---|---|
| 3,634,582 A | 1/1972 | Hartley et al. | |
| 3,860,618 A | 1/1975 | Hartley et al. | |
| 3,957,965 A | 5/1976 | Hartley et al. | |
| 4,042,700 A | 8/1977 | Banholzer et al. | |
| 4,608,377 A | 8/1986 | Banholzer et al. | |
| 4,783,534 A | 11/1988 | Banholzer | |
| 5,478,578 A | 12/1995 | Arnold et al. | |
| 5,498,422 A | 3/1996 | Nakamichi et al. | |
| 5,610,163 A | 3/1997 | Banholzer et al. | |
| 5,654,314 A | 8/1997 | Banholzer et al. | |
| 5,770,738 A | 6/1998 | Banholzer et al. | |
| 5,947,118 A | 9/1999 | Hochrainer et al. | |
| 5,952,505 A | 9/1999 | Banholzer | |
| 6,183,782 B1 | 2/2001 | Hallworth | |
| 6,221,338 B1 | 4/2001 | Staniforth | |
| 6,228,394 B1 * | 5/2001 | Horhota et al. | 424/456 |
| 6,235,725 B1 * | 5/2001 | Ahmed | 514/56 |
| 6,274,287 B1 | 8/2001 | Moriuma et al. | |
| 6,482,429 B1 | 11/2002 | Etzler | |
| 6,486,321 B1 | 11/2002 | Banholzer et al. | |
| 6,506,900 B1 | 1/2003 | Banholzer et al. | |
| 6,517,865 B1 | 2/2003 | Cade et al. | |
| 6,585,959 B1 | 7/2003 | Walz et al. | |
| 6,589,536 B1 | 7/2003 | Brox et al. | |
| 6,645,466 B1 | 11/2003 | Keller et al. | |
| 6,881,422 B1 | 4/2005 | Banholzer et al. | |
| 6,905,239 B1 | 6/2005 | Boeck et al. | |
| 2003/0043687 A1 | 3/2003 | Boeck et al. | |
| 2003/0068278 A1 | 4/2003 | Boeck et al. | |
| 2003/0070679 A1 | 4/2003 | Hochrainer et al. | |
| 2003/0125350 A1 | 7/2003 | Hassan et al. | |
| 2003/0202944 A1 | 10/2003 | Staniforth | |
| 2003/0235538 A1 | 12/2003 | Zierenberg | |
| 2004/0002510 A1 | 1/2004 | Bender et al. | |
| 2004/0002548 A1 | 1/2004 | Bozung et al. | |
| 2004/0029907 A1 | 2/2004 | Banholzer et al. | |
| 2004/0136919 A1 | 7/2004 | Hartig et al. | 424/46 |

FOREIGN PATENT DOCUMENTS

| | | |
|---|---|---|
| EP | 0 172 258 | 2/1985 |
| EP | 0 418 716 | 9/1990 |
| FR | 8.142 M A | 8/1970 |
| WO | WO 93/11746 A1 | 6/1993 |
| WO | WO 94/28956 | 12/1994 |
| WO | WO 95/11666 A1 | 5/1995 |
| WO | WO 95/24889 A1 | 9/1995 |
| WO | WO 96/02231 | 2/1996 |
| WO | WO 00/28979 A1 | 5/2000 |
| WO | WO 00/47200 A1 | 8/2000 |
| WO | WO 02/30389 | 4/2002 |
| WO | WO 02/098874 | 12/2002 |
| WO | WO 03/084502 | 10/2003 |
| WO | WO 03/084509 | 10/2003 |

OTHER PUBLICATIONS

Walz, M. et al; "Process for Preparing Powder Formulations"; USSN 09/977,911; Oct. 11, 2001.
U.S. Appl. No. 09/961,822; filed Sep. 24, 2001; Banholzer, et al.
N.H. Shah, et al. "Elasticity of Soft Gelatin Capsules Containing Polyethylene Glycol 400 –Quantitation and Resolution" Pharmaceutical Technology, pp. 126–133, Mar. 1992.
Mareke Hartig, et al. "New Tiotropium Containing Powder Formulation for Inhalation" New U.S. Appl. No. 10/718, 404, filed Nov. 20, 2003.

* cited by examiner

*Primary Examiner*—Carlos A. Azpuru
(74) *Attorney, Agent, or Firm*—Michael Morris; Mary-Ellen M. Devlin; Andrea D. Small

(57) ABSTRACT

The invention relates to powdered preparations containing tiotropium for inhalation, processes for preparing them as well as their use in preparing a pharmaceutical composition for the treatment of respiratory complaints, particularly for the treatment of COPD (chronic obstructive pulmonary disease) and asthma.

41 Claims, No Drawings

INHALABLE POWDER CONTAINING TIOTROPIUM

RELATED APPLICATIONS

The present application is a continuation of U.S. Ser. No. 10/396,179 now U.S. Pat. No. 6,743,437 which is a continuation of U.S. Ser. No. 09/982,219, filed Oct. 17, 2001 now U.S. Pat. No. 6,537,568 which is a continuation of U.S. Ser. No. 09/587,485, filed Jun. 5, 2000 now U.S. Pat. No. 6,306,426 which is a continuation-in-part of U.S. Ser. No. 09/356,074 filed Jul. 16, 1999, now U.S. Pat. No. 6,110,485 which is a continuation of U.S. Ser. No. 09/150,990 filed Sep. 10, 1998, now abandoned which is a continuation of U.S. Ser. No. 08/908,094 filed Aug. 11, 1997, now abandoned.

FIELD OF THE INVENTION

The invention relates to powdered preparations containing tiotropium for inhalation, processes for preparing them as well as their use for preparing a pharmaceutical composition for treating respiratory complaints, particularly for treating COPD (chronic obstructive pulmonary disease) and asthma.

BACKGROUND OF THE INVENTION

Tiotropium bromide is known from European Patent Application EP 418 716 A1 and has the following chemical structure:

Tiotropium bromide is a highly effective anticholinergic with a long-lasting activity which can be used to treat respiratory complaints, particularly COPD (chronic obstructive pulmonary disease) and asthma. The term tiotropium refers to the free ammonium cation.

For treating the abovementioned complaints, it is useful to administer the active substance by inhalation. In addition to the administration of broncholytically active compounds in the form of metered aerosols and inhalable solutions, the use of inhalable powders containing active substance is of particular importance.

With active substances which have a particularly high efficacy, only small amounts of the active substance are needed per single dose to achieve the desired therapeutic effect. In such cases, the active substance has to be diluted with suitable excipients in order to prepare the inhalable powder. Because of the large amount of excipient, the properties of the inhalable powder are critically influenced by the choice of excipient. When choosing the excipient its particle size is particularly important. As a rule, the finer the excipient, the poorer its flow properties. However, good flow properties are a prerequisite for highly accurate metering when packing and dividing up the individual doses of preparation, e.g. when producing capsules (inhalettes) for powder inhalation or when the patient is metering the individual dose before using a multi-dose inhaler. Moreover, the particle size of the excipient is very important for the emptying characteristics of capsules when used in an inhaler. It has also been found that the particle size of the excipient has a considerable influence on the proportion of active substance in the inhalable powder which is delivered for inhalation. The term inhalable proportion of active substance refers to the particles of the inhalable powder which are conveyed deep into the branches of the lungs when inhaled with a breath. The particle size required for this is between 1 and 10 μm, preferably less than 6 μm.

The aim of the invention is to prepare an inhalable powder containing tiotropium which, while being accurately metered (in terms of the amount of active substance and powder mixture packed into each capsule by the manufacturer as well as the quantity of active substance released and delivered to the lungs from each capsule by the inhalation process) with only slight variations between batches, enables the active substance to be administered in a large inhalable proportion. A further aim of the present invention is to prepare an inhalable powder containing tiotropium which ensures good emptying characteristics of the capsules, whether it is administered to the patient using an inhaler, for example, as described in WO 94/28958, or in vitro using an impactor or impinger.

The fact that tiotropium, particularly tiotropium bromide, has a therapeutic efficacy even at very low doses imposes further conditions on an inhalable powder which is to be used with highly accurate metering. Because only a low concentration of the active substance is needed in the inhalable powder to achieve the therapeutic effect, a high degree of homogeneity of the powder mixture and only slight fluctuations in the dispersion characteristics from one batch of capsules to the next are essential. The homogeneity of the powder mixture and minor fluctuations in the dispersion properties are crucial in ensuring that the inhalable proportion of active substance is released reproducibly in constant amounts and with the lowest possible variability.

Accordingly, a further aim of the present invention is to prepare an inhalable powder containing tiotropium which is characterised by a high degree of homogeneity and uniformity of dispersion. The present invention also sets out to provide an inhalable powder which allows the inhalable proportion of active substance to be administered with the lowest possible variability.

DETAILED DESCRIPTION OF THE INVENTION

It was found that, surprisingly, the objective outlined above can be achieved by means of the powdered preparations for inhalation (inhalable powders) according to the invention described hereinafter.

Accordingly, the present invention relates to inhalable powders containing 0.04 to 0.8% of tiotropium mixed with a physiologically acceptable excipient, characterised in that the excipient consists of a mixture of coarser excipient with an average particle size of 15 to 80 μm and finer excipient with an average particle size of 1 to 9 μm, the proportion of finer excipient representing 1 to 20% of the total amount of excipient. Inhalable powders which contain 0.08 to 0.64%, most preferably 0.16 to 0.4% of tiotropium, are preferred according to the invention.

By tiotropium is meant the free ammonium cation. The counter-ion (anion) may be chloride, bromide, iodide, methanesulphonate, para-toluenesulphonate or methyl sulphate. Of these anions, the bromide is preferred.

Accordingly, the present invention preferably relates to inhalable powders which contain between 0.048 and 0.96% of tiotropium bromide. Of particular interest according to the invention are inhalable powders which contain 0.096 to 0.77%, most preferably 0.19 to 0.48% of tiotropium bromide.

The tiotropium bromide which is preferably contained in the inhalable powders according to the invention may include solvent molecules during crystallisation. Preferably, the hydrates of tiotropium bromide, most preferably tiotropium bromide monohydrate, are used to prepare the tiotropium-containing inhalable powder according to the invention. Accordingly the present invention relates to powders for inhalation which contain between 0.05 and 1% of tiotropium bromide monohydrate. Of particular interest according to the invention are inhalable powders which contain 0.1 to 0.8%, most preferably 0.2 to 0.5% of tiotropium bromide monohydrate.

The inhalable powders according to the invention are preferably characterised in that the excipient consists of a mixture of coarser excipient with an average particle size of 17 to 50 µm, most preferably 20 to 30 µm, and finer excipient with an average particle size of 2 to 8 µm, most preferably 3 to 7 µm. The phrase average particle size used here denotes the 50% value from the volume distribution measured with a laser diffractometer using the dry dispersion method. Inhalable powders in which the proportion of finer excipient in the total amount of excipient is from 3 to 15%, most preferably 5 to 10%, are preferred.

The percentages given within the scope of the present invention are always percent by weight.

When reference is made to a mixture within the scope of the present invention, this always means a mixture obtained by mixing together clearly defined components. Accordingly, when an excipient mixture of coarser and finer excipients is mentioned, this can only denote mixtures obtained by mixing a coarser excipient component with a finer excipient component.

The coarser and finer excipient fractions may consist of chemically identical or chemically different substances, while inhalable powders in which the coarser excipient fraction and the finer excipient fraction consist of the same chemical compound are preferred.

Examples of physiologically acceptable excipients which may be used to prepare the inhalable powders according to the invention include, for example, monosaccharides (e.g. glucose or arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

The inhalable powders according to the invention may for example be administered using inhalers which meter a single dose from a reservoir by means of a measuring chamber (e.g. according to U.S. Pat. No. 4,570,630A) or by other means (e.g. according to DE 36 25 685 A). Preferably, however, the inhalable powders according to the invention are packed into capsules (to make so-called inhalettes), which are used in inhalers such as those described in WO 94/28958, for example.

If the inhalable powder according to the invention is to be packed into capsules (inhalettes) in accordance with the preferred application mentioned above, it is advisable to fill the capsules with amounts of from 3 to 10 mg, preferably from 4 to 6 mg of inhalable powder per capsule. These will then contain between 1.2 and 80 µg of tiotropium. With a preferred filling of 4 to 6 mg of inhalable powder per capsule, the content of tiotropium per capsule is between 1.6 and 48 µg, preferably between 3.2 and 38.4 µg, most preferably between 6.4 and 24 µg. A content of 18 µg of tiotropium, for example, corresponds to a content of about 21.7 µg of tiotropium bromide.

Consequently, capsules containing 3 to 10 mg of powder for inhalation preferably hold between 1.4 and 96.3 µg of tiotropium bromide, according to the invention. When the filling is from 4 to 6 mg of inhalable powder per capsule, as is preferred, each capsule contains between 1.9 and 57.8 µg, preferably between 3.9 and 46.2 µg, most preferably between 7.7 and 28.9 µg of tiotropium bromide. A content of 21.7 µg of tiotropium bromide, for example, corresponds to a content of about 22.5 µg of tiotropium bromide monohydrate.

Consequently, capsules containing 3 to 10 mg of powder for inhalation preferably hold between 1.5 and 100 µg of tiotropium bromide monohydrate. When the filling is from 4 to 6 mg of inhalable powder per capsule, as is preferred, each capsule contains between 2 and 60 µg, preferably between 4 and 48 µg, most preferably between 8 and 30 µg of tiotropium bromide monohydrate.

The inhalable powders according to the invention are characterised, in accordance with the objective on which the present invention is based, by a high degree of homogeneity in terms of the accuracy of metering of single doses. This is in the range of <8%, preferably <6%, most preferably <4%.

The inhalable powders according to the invention may be obtained by the method described hereinafter.

After the starting materials have been weighed out, first of all the excipient mixture is prepared from the defined fractions of the coarser excipient and finer excipient. Then the inhalable powder according to the invention is prepared from the excipient mixture and the active substance. If the inhalable powder is to be administered using inhalettes in suitable inhalers, the preparation of the inhalable powders is followed by the manufacture of the powder-filled capsules.

In the preparation processes described hereinafter, the abovementioned components are used in the amounts by weight described in the abovementioned compositions of the inhalable powders according to the invention.

The powders for inhalation according to the invention are prepared by mixing the coarser excipient fractions with the finer excipient fractions and subsequently mixing the resulting excipient mixtures with the active substance.

To prepare the excipient mixture, the coarser and finer excipient fractions are placed in a suitable mixing container. The two components are preferably added using a granulating sieve with a mesh size of 0.1 to 2 mm, preferably 0.3 to 1 mm, most preferably 0.3 to 0.6 mm. Preferably, the coarser excipient is put in first and then the finer excipient fraction is added to the mixing container. During this mixing process the two components are preferably added in batches, with some of the coarser excipient being put in first and then finer and coarser excipient being added alternately. It is particularly preferred when producing the excipient mixture to sieve in the two components in alternate layers. The two components are preferably sieved in alternately in 15 to 45, most preferably 20 to 40 layers each. The mixing of the two excipients may take place while the two components are still being added. Preferably, however, mixing is only done once the two components have been sieved in layer by layer.

Once the excipient mixture has been produced, this and the active substance are placed in a suitable mixing container. The active substance used has an average particle size of 0.5 to 10 μm, preferably 1 to 6 μm, most preferably 2 to 5 μm. The two components are preferably added using a granulating sieve with a mesh size of 0.1 to 2 mm, preferably 0.3 to 1 mm, most preferably 0.3 to 0.6 mm. Preferably, the excipient mixture is put in first and then the active substance is added to the mixing container. During this mixing process the two components are preferably added in batches. It is particularly preferred when producing the excipient mixture to sieve in the two components in alternate layers. The two components are preferably sieved in alternately in 25 to 65, most preferably 30 to 60 layers. The mixing of the excipient mixture with the active substance may take place while the two components are still being added. Preferably, however, mixing is only done once the two components have been sieved in layer by layer.

The powder mixture thus obtained may optionally be added once or repeatedly using a granulating sieve and then subjected to another mixing process.

One aspect of the present invention relates to an inhalable powder containing tiotropium, which may be obtained by the methods described hereinbefore.

When the term active substance is used within the scope of the present invention, this is intended as a reference to tiotropium. According to the invention, any reference to tiotropium, which is the free ammonium cation, corresponds to a reference to tiotropium in the form of a salt (tiotropium salt) which contains an anion as the counter-ion. Tiotropium salts which may be used within the scope of the present invention are those compounds which contain chloride, bromide, iodide, methanesulphonate, para-toluenesulphonate or methyl sulphate, in addition to tiotropium as counter-ion (anion). Within the scope of the present invention, tiotropium bromide is preferred of all the tiotropium salts. References to tiotropium bromide within the scope of the present invention should always be taken as references to all possible amorphous and crystalline modifications of tiotropium bromide. These may, for example, include molecules of solvent in their crystalline structure. Of all the crystalline modifications of tiotropium bromide, those which also include water (hydrates) are preferred according to the invention. It is particularly preferable to use tiotropium bromide monohydrate within the scope of the present invention.

In order to prepare the formulations according to the invention, first of all tiotropium has to be prepared in a form which can be used for pharmaceutical purposes. For this, tiotropium bromide, which may be prepared as disclosed in EP 418 716 A1, is preferably subjected to another crystallisation step. Depending on the reaction conditions and solvent used, different crystal modifications are obtained. These modifications may be told apart, for example, by DSC (Differential Scanning Calorimetry).

The following Table summarises the melting points of different crystal modifications of tiotropium bromide depending on the solvent, which are determined by DSC.

| solvent | DSC |
|---|---|
| methanol | 228° C. |
| ethanol | 227° C. |
| ethanol/water | 229° C. |

-continued

| solvent | DSC |
|---|---|
| water | 230° C. |
| isopropanol | 229° C. |
| acetone | 225° C. |
| ethyl acetate | 228° C. |
| tetrahydrofuran | 228° C. |

Tiotropium bromide monohydrate has proved particularly suitable for preparing the formulation according to the invention. The DSC diagram of tiotropium bromide monohydrate shows two characteristic signals. The first, relatively broad, endothermic signal between 50–120° C. can be attributed to the dehydration of the tiotropium bromide monohydrate to produce the anhydrous form. The second, relatively sharp endothermic peak at 230±5° C. can be put down to the melting of the substance. These data were obtained using a Mettler DSC 821 and evaluated with the Mettler STAR software package. These data, like the other values given in the above Table, were obtained at a heating rate of 10 K/min.

The following Examples serve to illustrate the present invention further without restricting its scope to the embodiments provided hereinafter by way of example.

Starting Materials

In the Examples which follow, lactose-monohydrate (200M) is used as the coarser excipient. It may be obtained, for example, from Messrs DMV International, 5460 Veghel/NL under the product name Pharmatose 200M.

In the Examples which follow, lactose-monohydrate (5μ) is used as the finer excipient. It may be obtained from lactose-monohydrate 200M by conventional methods (micronising). Lactose-monohydrate 200M may be obtained, for example, from Messrs DMV International, 5460 Veghel/NL under the product name Pharmatose 200M.

Preparation of Tiotropium Bromide Monohydrate 15.0 kg of tiotropium bromide are added to 25.7 kg of water In a suitable reaction vessel. The mixture is heated to 80–90° C. and stirred at constant temperature until a clear solution is formed. Activated charcoal (0.8 kg), moistened with water, is suspended in 4.4 kg of water, this mixture is added to the solution containing the tiotropium bromide and rinsed with 4.3 kg of water. The mixture thus obtained is stirred for at least 15 min at 80–90° C. and then filtered through a heated filter into an apparatus which has been preheated to an outer temperature of 70° C. The filter is rinsed with 8.6 kg of water. The contents of the apparatus are cooled at 3–5° C. every 20 minutes to a temperature of 20–25° C. The apparatus is further cooled to 10–15° C. using cold water and crystallisation is completed by stirring for at least one hour. The crystals are isolated using a suction drier, the crystal slurry isolated is washed with 9 liters of cold water (10–15° C.) and cold acetone (10–15° C.). The crystals obtained are dried in a nitrogen current at 25° C. over 2 hours. Yield: 13.4 kg of tiotropium bromide monohydrate (86% of theory)

The crystalline tiotropium bromide monohydrate thus obtained is micronised by known methods, to bring the active substance into the average particle size which meets the specifications according to the invention.

The method of determining the average particle size of the various ingredients of the formulation according to the invention is described as follows.

A) Determining the particle size of finely divided lactose:

Measuring Equipment and Settings

The equipment is operated according to the manufacturer's instructions.

| | |
|---|---|
| Measuring equipment: | HELOS Laser-diffraction spectrometer, (SympaTec) |
| Dispersing unit: | RODOS dry disperser with suction funnel, (SympaTec) |
| Sample quantity: | from 100 mg |
| Product feed: | Vibri Vibrating channel, Messrs. Sympatec |
| Frequency of vibrating channel: | 40 rising to 100% |
| Duration of sample feed: | 1 to 15 sec. (in the case of 100 mg) |
| Focal length: | 100 mm (measuring range: 0.9–175 µm) |
| Measuring time: | about 15 s (in the case of 100 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed

At least 100 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The time taken to feed in the entire sample is 10 to 15 sec.

B) Determining the particle size of micronised tiotropium bromide monohydrate:

Measuring Equipment and Settings

The equipment is operated according to the manufacturer's instructions.

| | |
|---|---|
| Measuring equipment: | Laser diffraction spectrometer (HELOS), Sympatec |
| Dispersing unit: | RODOS dry disperser with suction funnel, Sympatec |
| Sample quantity: | 50 mg–400 mg |
| Product feed: | Vibri Vibrating channel, Messrs. Sympatec |
| Frequency of vibrating channel: | 40 rising to 100% |
| Duration of sample feed: | 15 to 25 sec. (in the case of 200 mg) |
| Focal length: | 100 mm (measuring range: 0.9–175 µm) |
| Measuring time: | about 15 s (in the case of 200 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed

About 200 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The sample should be fed in as continuously as possible. However, the amount of product should not be so great that adequate dispersion cannot be achieved. The time over which the entire sample is fed in is about 15 to 25 seconds for 200 mg, for example.

C) Determining the particle size of lactose 200M

Measuring Equipment and Settings

The equipment is operated according to the manufacturer's instructions.

| | |
|---|---|
| Measuring equipment: | Laser diffraction spectrometer (HELOS), Sympatec |
| Dispersing unit: | RODOS dry disperser with suction funnel, Sympatec |
| Sample quantity: | 500 mg |
| Product feed: | VIBRI Vibrating channel, Messrs. Sympatec |
| Frequency of vibrating channel: | 18 rising to 100% |
| Focal length (1): | 200 mm (measuring range: 1.8–350 µm) |
| Focal length (2): | 500 mm (measuring range: 4.5–875 µm) |
| Measuring time: | 10 s |
| Cycle time: | 10 ms |
| Start/stop at: | 1% on channel 19 |
| Pressure: | 3 bar |
| Vacuum: | maximum |
| Evaluation method: | HRLD |

Sample Preparation/Product Feed

About 500 mg of the test substance are weighed onto a piece of card. Using another piece of card all the larger lumps are broken up. The powder is then transferred into the funnel of the vibrating channel. A gap of 1.2 to 1.4 mm is set between the vibrating channel and funnel. After the start of the measurement the amplitude setting of the vibrating channel is increased from 0 to 40% until a continuous flow of product is obtained. Then it is reduced to an amplitude of about 18%. Towards the end of the measurement the amplitude is increased to 100%.

Apparatus

The following machines and equipment, for example, may be used to prepare the inhalable powders according to the invention:

Mixing container or powder mixer: Gyrowheel mixer 200 L; type: DFW80N-4; made by:

Messrs Engelsmann, D-67059 Ludwigshafen.

Granulating sieve: Quadro Comil; type: 197-S; made by: Messrs Joisten & Kettenbaum, D-51429 Bergisch-Gladbach.

EXAMPLE 1

1.1: Excipient Mixture 31.82 kg of lactose monohydrate for inhalation (200M) are used as the coarser excipient component. 1.68 kg of lactose monohydrate (5 μm) are used as the finer excipient component. In the resulting 33.5 kg of excipient mixture the proportion of the finer excipient component is 5%.

About 0.8 to 1.2 kg of lactose monohydrate for inhalation (200M) are added to a suitable mixing container through a suitable granulating sieve with a mesh size of 0.5 mm. Then alternate layers of lactose monohydrate (5 μm) in batches of about 0.05 to 0.07 kg and lactose monohydrate for inhalation (200M) in batches of 0.8 to 1.2 kg are sieved in. Lactose monohydrate for inhalation (200M) and lactose monohydrate (5 μm) are added in 31 and 30 layers, respectively (tolerance:±6 layers).

The ingredients sieved in are then mixed together (mixing at 900 rpm).

1.2: Final Mixture

To prepare the final mixture, 32.87 kg of the excipient mixture (1.1) and 0.13 kg of micronised tiotropium bromide monohydrate are used. The content of active substance in the resulting 33.0 kg of inhalable powder is 0.4%.

About 1.1 to 1.7 kg of excipient mixture (1.1) are added to a suitable mixing container through a suitable granulating sieve with a mesh size of 0.5 mm. Then alternate layers of tiotropium bromide monohydrate in batches of about 0.003 kg and excipient mixture (1.1) in batches of 0.6 to 0.8 kg are sieved in. The excipient mixture and the active substance are added in 46 or 45 layers, respectively (tolerance:±9 layers).

The ingredients sieved in are then mixed together (mixing at 900 rpm). The final mixture is passed through a granulating sieve twice more and then mixed (mixing at 900 rpm).

EXAMPLE 2

| Inhalation capsules (inhalettes) having the following composition were produced using the mixture obtained according to Example 1: | |
|---|---|
| tiotropium bromide monohydrate: | 0.0225 mg |
| lactose monohydrate (200 M): | 5.2025 mg |
| lactose monohydrate (5 μm): | 0.2750 mg |
| hard gelatine capsule: | 49.0 mg |
| Total: | 54.5 mg |

EXAMPLE 3:

| Inhalation capsules having the composition: | |
|---|---|
| tiotropium bromide monohydrate: | 0.0225 mg |
| lactose monohydrate (200 M): | 4.9275 mg |
| lactose monohydrate (5 μm): | 0.5500 mg |
| hard gelatine capsule: | 49.0 mg |
| Total: | 54.5 mg |

The inhalable powder needed to prepare the capsules was obtained analogously to Example 1.

Example 4:

| Inhalation capsules having the composition: | |
|---|---|
| tiotropium bromide monohydrate: | 0.0225 mg |
| lactose monohydrate (200 M): | 5.2025 mg |
| lactose monohydrate (5 μm): | 0.2750 mg |
| polyethylene capsule: | 100.0 mg |
| Total: | 105.50 mg |

The inhalable powder needed to prepare the capsules was obtained analogously to Example 1.

For the purposes of the present invention the mean particle size denotes the value in μm at which 50% of the particles from the volume distribution have a particle size which is smaller than or equal to the value specified. Laser diffraction/dry dispersion is used as the method of measurement for determining the total distribution of the particle size distribution.

We claim:

1. An inhalable powder comprising 0.04 to 0.8% of tiotropium in admixture with a physiologically acceptable excipient, wherein the excipient consists of a mixture of coarser excipient with an average particle size of 15 to 80 μm and finer excipient with an average particle size of 1 to 9 μm, the proportion of the finer excipient constituting 1 to 20% of the total amount of excipient, wherein the inhalable proportion of active substance is released reproducibly in low variability amounts when administered to a patent.

2. An inhalable powder according to claim 1, wherein the tiotropium is present in the form of the chloride, bromide, iodide, methanesulphonate, para-toluenesulphonate or methyl sulphate thereof.

3. An inhalable powder comprising between 0.048 and 0.96% of tiotropium bromide in admixture with a physiologically acceptable excipient, wherein the excipient consists of a mixture of coarser excipient with an average particle size of 15 to 80 μm and finer excipient with an average particle size of 1 to 9 μm, the proportion of the finer excipient constituting 1 to 20% of the total amount of excipient, wherein the inhalable proportion of active substance is released reproducibly in low variability amounts when administered to a patent.

4. An inhalable powder comprising between 0.05 and 1% of tiotropium bromide monohydrate in admixture with a physiologically acceptable excipient, wherein the excipient consists of a mixture of coarser excipient with an average particle size of 15 to 80 μm and finer excipient with an average particle size of 1 to 9 μm, the proportion of the finer excipient constituting 1 to 20% of the total amount of excipient, wherein the inhalable proportion of active substance is released reproducibly in low variability amounts when administered to a patent.

5. An inhalable powder according to one of claims 1, 2, 3 or 4, wherein the excipient consists of a mixture of coarser excipient with an average particle size of 17 to 50 μm and finer excipient with an average particle size of 2 to 8 μm.

6. An inhalable powder according to one of claims 1, 2, 3 or 4, wherein the proportion of finer excipient in the total amount of excipient is 3 to 15%.

7. An inhalable powder according to one of claims 1, 2, 3 or 4, wherein the tiotropium used has an average particle size of 0.5 to 10 μm.

8. An inhalable powder according to one of claims 1, 2, 3 or 4, wherein one or more monosaccharides, disaccharides, oligo- or polysaccharides, polyalcohols, salts thereof, or mixtures thereof are used as the excipients.

9. An inhalable powder according to claim 8, wherein glucose, arabinose, lactose, saccharose, maltose, dextrane, sorbitol, mannitol, xylitol, sodium chloride, calcium carbonate or mixtures thereof are used as the excipients.

10. An inhalable powder according to claim 9, wherein glucose or lactose or mixtures thereof are used as the excipients.

11. A process for preparing an inhalable powder according to one of claims 1 to 4, comprising: (a) mixing coarser excipient fractions with finer excipient fractions to obtain an excipient mixture, and (b) mixing the excipient mixture thus obtained with the tiotropium.

12. A method of treating a disease that is responsive to the administration of tiotropium, comprising administering to a host in need thereof an inhalable powder according to one of claims 1 to 4 or 12.

13. A method according to claim 12, wherein the disease is asthma or COPD.

14. An inhalable powder according to claim 4 comprising 0.1 to 0.8% of tiotropium bromide monohydrate.

15. An inhalable powder according to claim 4 comprising 0.2 to 0.5% of tiotropium bromide monohydrate.

16. An inhalable powder according to one of claim 1, 2, 3 or 4, wherein the excipient consists of a mixture of coarser excipient with an average particle size of 20 to 30 μm and finer excipient with an average particle size of 3 to 7 μm.

17. An inhalable powder according to one of claim 1, 2, 3 or 4, wherein the proportion of finer excipient in the total amount of excipient is 5 to 10%.

18. An inhalable powder according to one of claim 1, 2, 3 or 4, wherein the tiotropium used has an average particle size of 1 to 6 μm.

19. An inhalable powder according to one of claim 1, 2, 3 or 4, wherein the tiotropium used has an average particle size of 2 to 5 μm.

20. An inhalable powder according to claim 10, wherein lactose monohydrate is used as the excipient.

21. An inhalable powder comprising between 0.2 and 0.5% of tiotropium bromide monohydrate in admixture with lactose monohydrate as the physiologically acceptable excipient, wherein the excipient consists of a mixture of coarser excipient with an average particle size of 20 to 30 μm and finer excipient with an average particle size of 3 to 7 μm, the proportion of the finer excipient constituting 5 to 10% of the total amount of excipient, wherein the inhalable proportion of active substance is released reproducibly in low variability amounts when administered to a patent.

22. An inhalable powder comprising 0.04 to 0.8% of tiotropium in admixture with a physiologically acceptable excipient, said inhalable powder prepared by a process comprising: (a) mixing coarser excipient having an average particle size of 15 to 80 μm and finer excipient having an avenge particle size of 1 to 9 μm, wherein the proportion of the finer excipient constitutes 1 to 20% of the total amount of excipient, to obtain an excipient mixture, and (b) mixing the excipient mixture thus obtained with the tiotropium, wherein the inhalable proportion of active substance is released reproducibly in low variability amounts when administered to a patent.

23. An inhalable powder according to claim 22, wherein the tiotropium is present in the form of the chloride, bromide, iodide, methanesulphonate, para-toluenesulphonate or methyl sulphate thereof.

24. An inhalable powder comprising between 0.048 and 0.96% of tiotropium bromide in admixture with a physiologically acceptable excipient, said inhalable powder prepared by a process comprising: (a) mixing coarser excipient having an average particle size of 15 to 80 μm and finer excipient having an average particle size of 1 to 9 μm, wherein the proportion of the finer excipient constitutes 1 to 20% of the total amount of excipient, to obtain an excipient mixture, and (b) mixing the excipient mixture thus obtained with the tiotropium bromide, wherein the inhalable proportion of active substance is released reproducibly in low variability amounts when administered to a patent.

25. An inhalable powder comprising between 0.05 and 1% of tiotropium bromide monohydrate in admixture with a physiologically acceptable excipient, said inhalable powder prepared by a process comprising: (a) mixing coarser excipient having an average particle size of 15 to 80 μm and finer excipient having an average particle size of 1 to 9 μm, wherein the proportion of the finer excipient constitutes 1 to 20% of the total amount of excipient, to obtain an excipient mixture, and (b) mixing the excipient mixture thus obtained with the tiotropium bromide monohydrate, wherein the inhalable proportion of active substance is released reproducibly in low variability amounts when administered to a patent.

26. An inhalable powder according to claim 25 comprising 0.1 to 0.8% of tiotropium bromide monohydrate.

27. An inhalable powder according to claim 25 comprising 0.2 to 0.5% of tiotropium bromide monohydrate.

28. An inhalable powder according to one of claim 22, 23, 24 or 25, wherein the coarser excipient has an average particle size of 17 to 50 μm and the finer excipient has an average particle size of 2 to 8 μm.

29. An inhalable powder according to one of claim 22, 23, 24 or 25, wherein the coarser excipient has an average particle size of 20 to 30 μm and the finer excipient has an average particle size of 3 to 7 μm.

30. An inhalable powder according to one of claim 22, 23, 24 or 25, wherein the proportion of finer excipient in the total amount of excipient is 3 to 15%.

31. An inhalable powder according to one of claim 22, 23, 24 or 25, wherein the proportion of finer excipient in the total amount of excipient is 5 to 10%.

32. An inhalable powder according to one of claim 22, 23, 24 or 25, wherein the tiotropium used has an average particle size of 0.5 to 10 μm.

33. An inhalable powder according to one of claim 22, 23, 24 or 25, wherein the tiotropium used has an average particle size of 1 to 6 μm.

34. An inhalable powder according to one of claim 22, 23, 24 or 25, wherein the tiotropium used has an average particle size of 2 to 5 μm.

35. An inhalable powder according to one of claim 22, 23, 24 or 25, wherein one or more monosaccharides, disaccharides, oligo- or polysaccharides, polyalcohols, salts thereof, or mixtures thereof are used as the excipients.

36. An inhalable powder according to claim 35, wherein glucose, arabinose, lactose, saccharose, maltose, dextrane, sorbitol, mannitol, xylitol, sodium chloride, calcium carbonate or mixtures thereof are used as the excipients.

37. An inhalable powder according to claim 36, wherein glucose or lactose or mixtures thereof are used as the excipients.

38. An inhalable powder according to claim 37, wherein lactose monohydrate is used as the excipient.

39. An inhalable powder comprising between 0.2 and 0.5% of tiotropium bromide monohydrate in admixture with lactose monohydrate as a physiologically acceptable excipient, said inhalable powder prepared by a process comprising: (a) mixing coarser lactose monohydrate excipient having an average particle size of 20 to 30 μm and finer lactose monohydrate excipient having an average particle size of 3 to 7 μm, wherein the proportion of the finer lactose monohydrate excipient constitutes 5 to 10% of the total amount of excipient, to obtain an excipient mixture, and (b) mixing the excipient mixture thus obtained with the tiotropium bromide monohydrate, wherein the inhalable proportion of active substance is released reproducibly in low variability amounts when administered to a patent.

40. A method of treating a disease that is responsive to the administration of tiotropium, comprising administering to a host in need thereof an inhalable powder according to one of claim 22, 23, 24 or 25 or 39.

41. A method according to claim 40, wherein the disease is asthma or COPD.

* * * * *

UNITED STATES PATENT AND TRADEMARK OFFICE
CERTIFICATE OF CORRECTION

PATENT NO. : 7,070,800 B2 Page 1 of 1
APPLICATION NO. : 09/975418
DATED : July 4, 2006
INVENTOR(S) : Karoline Bechtold-Peters et al.

It is certified that error appears in the above-identified patent and that said Letters Patent is hereby corrected as shown below:

In column 10, line 15 delete "patent" and replace with --patient--.

Signed and Sealed this

Eighth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 7,070,800 B2 Page 1 of 1
APPLICATION NO. : 09/975418
DATED : July 4, 2006
INVENTOR(S) : Karin Bechtold Peters et al.

It is certified that error appears in the above-identified patent and that said Letters Patent is hereby corrected as shown below:

In column 10, line 29, delete "patent" and replace with --patient--

In column 10, line 39, delete "patent" and replace with --patient--

In column 11, line 32, delete "patent" and replace with --patient--

In column 11, line 43, delete "patent" and replace with --patient--

In column 11, line 58, delete "patent" and replace with --patient--

In column 12, line 6, delete "patent" and replace with --patient--

In column 12, line 57, delete "patent" and replace with --patient--

Signed and Sealed this

Twelfth Day of August, 2008

JON W. DUDAS
*Director of the United States Patent and Trademark Office*